United States Patent [19]

Johnson et al.

[11] Patent Number: 4,563,633
[45] Date of Patent: Jan. 7, 1986

[54] APPARATUS FOR SENSING OPENINGS IN SHEET

[75] Inventors: Ken R. Johnson, Granville; Paul S. Sanik, Westerville, both of Ohio

[73] Assignee: Owens-Corning Fiberglas Corporation, Toledo, Ohio

[21] Appl. No.: 493,540

[22] Filed: May 11, 1983

[51] Int. Cl.[4] .................................. G01R 31/12
[52] U.S. Cl. ............................ 324/54; 200/61.13; 340/675
[58] Field of Search .................. 324/54, 65 P; 200/61.13, 61.14, DIG. 11; 340/675; 26/74, 70

[56] References Cited

U.S. PATENT DOCUMENTS

| | | | |
|---|---|---|---|
| 1,407,693 | 2/1922 | Heany | 324/54 |
| 2,748,381 | 5/1956 | Baker | 200/61.13 X |
| 2,873,425 | 2/1959 | Huggins | 340/675 X |
| 2,878,636 | 3/1959 | Fountain | 324/54 |
| 2,978,637 | 4/1961 | Price et al. | 324/54 |

Primary Examiner—Stanley T. Krawczewicz
Attorney, Agent, or Firm—Ronald C. Hudgens; Patrick P. Pacella; Thomas F. McGann

[57] ABSTRACT

An apparatus and method of sensing openings in a perforated sheet by means of electrical contact between electrically conducting surfaces positioned on opposite sides of the sheet.

12 Claims, 8 Drawing Figures

APPARATUS FOR SENSING OPENINGS IN SHEET

TECHNICAL FIELD

This invention pertains to the production of composite panels of roof insulation. The composite comprises a lower layer of fibrous glass board, an upper layer of foamed-in-place plastic foam, and a perforated plastic sheet disposed between the lower and upper layers. In one of its more specific aspects, this invention relates to an apparatus for sensing openings in the perforated plastic sheet and translating the sensor-collected data to useable inspection, and quality and process control form.

BACKGROUND OF THE INVENTION

The openings in the plastic sheet allow penetration of the plastic foam into the fibrous board to effect intermittent-site bonding of the board to the foam layer. If the openings are too numerous or too large, too much foam penetrates the fibrous glass board, raising the materials cost unnecessarily. If the openings are too few, too small, or improperly sited, too little foam penetrates the fibrous glass board, lowering the bonding efficiency and strength of the composite.

A need exists for an inspection apparatus to determine the deployment of the openings in a sheet, preferably a plastic sheet, before the sheet contacts the liquid foam, and a means to translate the deployment data to useable inspection, and quality and process control form.

Sensing of openings in sheets, cards, and tapes is well-known. Examples include player piano rolls, business machine punched cards, and teletype punched tape. The perforated sheet used in composite panels of roof insulation presents particular problems in sensing of openings in the sheet. The openings are about 0.040 inch in diameter and are spaced on about 0.5 inch centers. Accordingly, about one-half-of one percent of the surface of the sheet is comprised of openings. Optical and pneumatic sensors are incapable of sufficient resolution to sense deployment differences for such small holes, and are adversely affected by even slight misalignments of the sheet. Mechanical contacts such as fingers or probes are undesirably complicated for a sheet with such small holes at any significant machine speed. Additionally, sheet durability and misalignment sensitivity militate against use of mechanical contacts. The need demands a sensing apparatus comprising a large sensing field that is not adversely affected by sheet alignment, opening deployment, or high machine speed.

STATEMENT OF THE INVENTION

According to this invention there is provided an apparatus for sensing electrically, openings in a perforated sheet. The apparatus comprises two opposed, electrically conducting surfaces urgable toward each other to form a nip region in which lies, or through which is passed, a perforated sheet. At least one of the surfaces is sufficiently elastic to make electrical contact with the other surface through each opening. A signal generating means is provided to generate a signal in response to the electrical contact between the surfaces.

In one embodiment of the invention, the apparatus senses a plurality of reoccurring openings in the sheet.

In another embodiment of the invention, the apparatus senses openings in a moving sheet.

In a preferred embodiment of the invention, at least one of the opposing surfaces is moveable.

In another embodiment of the invention, means are provided for generating a second signal in the event that the first signal generated deviates from a predetermined pattern or value.

In an additional embodiment of the invention, at least one surface is divided into electrically-isolated parallel lanes.

DESCRIPTION OF THE INVENTION

Figure 1:
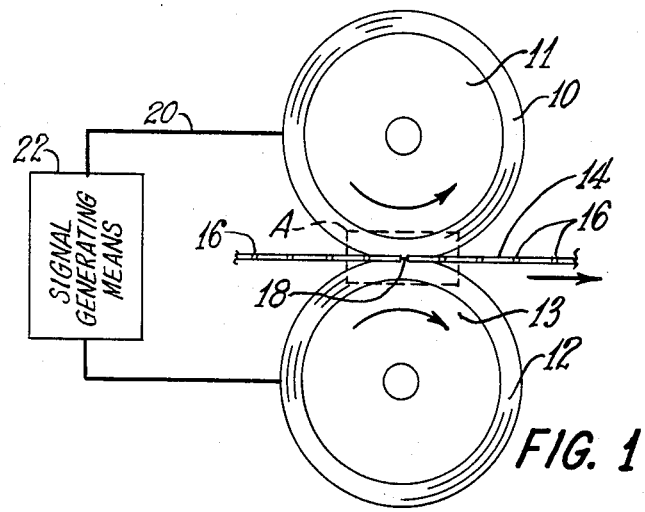
FIG. 1 is a schematic view of the apparatus of this invention.
Figure 1A:
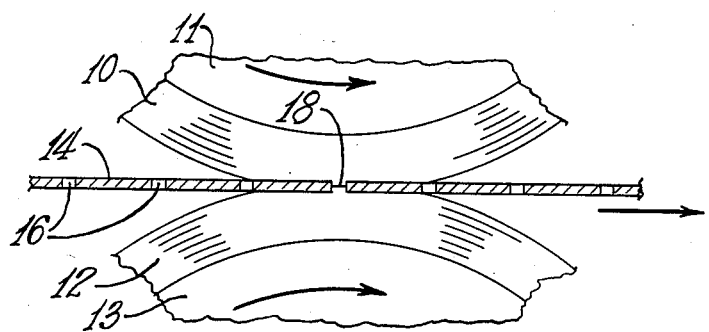
FIG. 1A is an enlarged view of the nip region.

As shown in FIG. 1, top surface 10, an elastic, continuous, electrically conducting surface is urged toward bottom surface 12, also an elastic, continuous, electrically conducting surface, to form a nip region A through which perforated sheet 14 having openings 16 therein, passes. As each opening 16 in the sheet passes through the nip region, the elastic top and bottom surfaces extrude through the opening and make electrical contact with each other at 18. This contact completes electrical circuit 20 generating a pulse which energizes signal generating means 22. As the perforated sheet moves through the nip region, a stream of pulses is generated as the surfaces make contact through the openings in the sheet, and no pulse will be generated as nonperforated sections of the sheet pass through the nip region. It can be seen that the instantaneous strength of the generated pulse is directly proportional to the size and number of openings 16 through which the top and bottom surfaces make electrical contact at a particular instant. The pulse-induced signal can be used for inspection, and quality and process control purposes in conjunction with devices such as an audible or visual alarms, CRT, recorders, product marking equipment, machine shut-off, or a retriggerable monostable multivibrator.

Signal generating means 22 can involve two separate signal generating means, examples of which are:

first signal generating means—TEXAS INSTRUMENTS—Monolithic Analog Level Detector—Device TL-490—Bulletin CL-410 (1979).

second signal generating means—MOTOROLA—Dual Precision Retriggerable/Resettable Monostable Multivibrator—MC1453B—Publication Series C (1978).

The invention will be discussed in terms of the best mode, viz two rotatable drums as the conducting surfaces, and a moving sheet, without meaning to limit the invention thereto.

Figure 2:
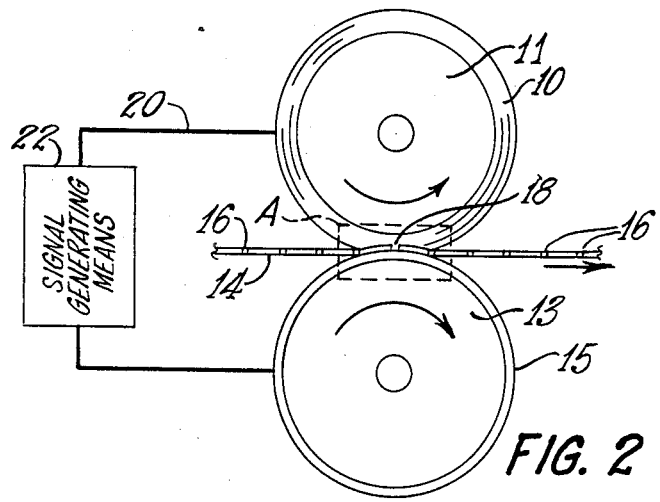
FIG. 2 is a schematic view of an additional embodiment of the invention comprising one elastic and one nonelastic conducting surface.

Top drum 11 and bottom drum 13 are of any suitable size and are urged toward each other by any suitable means such as mechanical or hydraulic devices, or by gravity. Each of the surfaces 10 and 12 compromise an elastic, electrically conducting material such as semiconducting silicone rubber. An example of such a material is TUFEL Silicone Rubber SE876 manufactured by General Electric Company. The elastic, electrically conducting material is adhered to the drums, preferably metallic drums. As shown in FIG. 2, it is also possible to construct the apparatus so that one surface comprises an elastic, electrically conducting material, and the other surface comprises a nonelastic, conducting material such as a steel drum surface 15. This configuration would be suitable for use with thin sheets.

Perforated sheet 14 can be any electrically nonconducting material such as plastic, fabric, or paper. It can be transparent, translucent or opaque, flexible or rigid.

Figure 3:
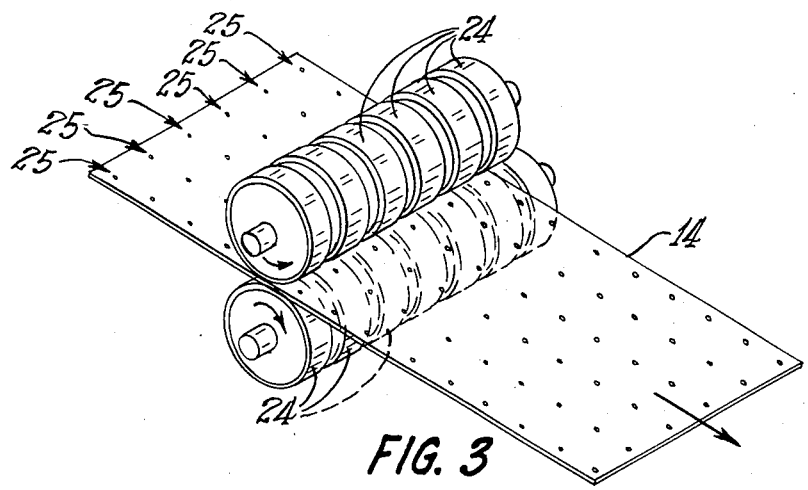
FIG. 3 is a perspective view of an additional embodiment of the invention comprising electrically-isolated surfaces.

FIG. 3 shows two rotatable drums, the elastic, electrically conducting surfaces of both of which are divided into electrically-isolated circumferential segments or lanes 24. Each drum lane registers with a lane of openings 25 in the sheet so that discreet signals are generated through each pair of opposing drum lane surfaces for each lane of openings. It is also possible to generate discreet signals for each lane of openings by employing one surface divided into electrically-isolated lanes, and one undivided, electrically-homogeneous surface.

Figure 4A:
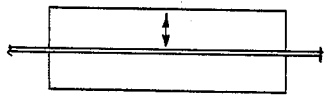
FIGS. 4A–4D present schematic views of a number of embodiments of the sensing surfaces and the perforated sheet.

FIG. 4 shows additional embodiments of the sensing surfaces and their interactions with the sheet:

FIG. 4A—two, flat, stationary surfaces and a stationary sheet.

Figure 4B:
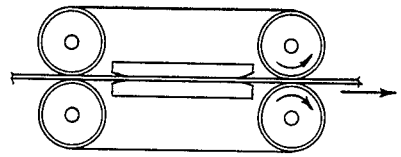

FIG. 4B—two flat, moving surfaces and a moving sheet.

Figure 4C:
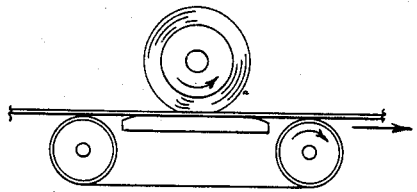

FIG. 4C—one round, moving surface, one flat moving surface, and a moving sheet.

Figure 4D:
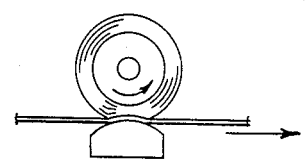

FIG. 4D—one round, moving surface, one arcuate stationary surface, and a moving sheet.

Variations in surface coupling, and use of electrically-isolated lanes described earlier are also possible in these additional embodiments.

Apparatus sensing speed, sheet width and thickness, and opening sizes and density are limited only by the properties of the materials used in constructing the apparatus, and the physical properties of the sheet.

It will be evident from the foregoing that various modifications can be made in the apparatus of this invention. Such, however, are within the scope of the invention.

We claim:

1. An apparatus for sensing openings in a sheet comprising:
    (a) two continuous, electrically conducting surfaces located in an electrical circuit and disposed on opposite sides of and in contact with said sheet, means for urging at least one of said surfaces toward the other said surface, at least one of said surfaces being sufficiently elastic to extend through said openings in said sheet to make electrical contact with the other said surface thereby completing said electrical circuit and generating an electrical first signal, the instantaneous strength of each said first signal being proportional to the size and number of said openings sensed at a particular instant, and
    (b) means for generating a second signal in the event that said first signal deviates from a predetermined signal pattern or value.

2. The apparatus of claim 1 wherein there is relative motion between said sheet and at least one of said surfaces.

3. The apparatus of claim 2 wherein at least one of said surfaces is on a rotating drum.

4. The apparatus of claim 1 wherein at least one of said surfaces is divided into two or more lanes, each of said lanes comprising a discrete said electrical circuit.

5. The apparatus of claim 4 wherein each of said lanes is oriented widthwise of said sheet.

6. The apparatus of claim 4 wherein each of said lanes is oriented lengthwise of said sheet.

7. The apparatus of claim 4 wherein there is relative motion between said sheet and at least one of said surfaces.

8. The apparatus of claim 7 wherein each of said lanes is oriented widthwise of said sheet.

9. The apparatus of claim 7 wherein each of said lanes is oriented lengthwise of said sheet.

10. The apparatus of claim 7 wherein at least one of said surfaces is on a rotating drum.

11. The apparatus of claim 10 wherein each of said lanes is oriented widthwise of said sheet.

12. The apparatus of claim 10 wherein each of said lanes is oriented lengthwise of said sheet.

* * * * *